United States Patent [19]

Mercier

[11] Patent Number: 4,933,501
[45] Date of Patent: Jun. 12, 1990

[54] PROCESS FOR THE PREPARATION OF TERPENE PEROXIDES AND PEROXIDES THUS OBTAINED

[75] Inventor: Claude Mercier, Lyons, France

[73] Assignee: Rhone-Poulenc Sante, Antony, France

[21] Appl. No.: 311,047

[22] Filed: Feb. 16, 1989

[30] Foreign Application Priority Data

Feb. 18, 1988 [FR] France ............................. 88 01920

[51] Int. Cl.⁵ .................. C07C 178/00; C07C 179/06
[52] U.S. Cl. .................................................. 568/558
[58] Field of Search ..................... 568/558, 568, 560

[56] References Cited

U.S. PATENT DOCUMENTS

2,516,649  7/1950  Rust et al. ............................ 568/558
4,133,835  1/1979  Bafford et al. ....................... 568/558

FOREIGN PATENT DOCUMENTS

658522 10/1951 United Kingdom .
767615  2/1957 United Kingdom .

OTHER PUBLICATIONS

J. Org. Chem., vol. 51, No. 10, 1986, pp. 1790–1793.
Tetrahedron, vol. 41, No. 19, 1985, pp. 4047–4056.
Journal of Organic Chemistry of the USSR, vol. 23, No. 9, partie Sep. 1, 1987, pp. 1640–1642.

*Primary Examiner*—Donald B. Moyer
*Assistant Examiner*—Karen E. Plue
*Attorney, Agent, or Firm*—Stevens, Davis, Miller & Mosher

[57] ABSTRACT

Terpene peroxides of formula:

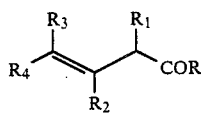

in which R denotes a tertiary alkyl radical substituted, if desired, by one or more phenyl radicals, a cycloalkyl radical or a trialkylsilyl radical, $R_1$, $R_2$ and $R_3$, which are identical or different, each denote hydrogen or an aliphatic radical optionally containing one or more double or triple bonds and optionally substituted, and $R_4$ denotes an aliphatic radical optionally containing one or more double or triple bonds and optionally substituted or $R_3$ denotes hydrogen and $R_2$ and $R_4$ together form an alkylene radical which may be substituted by one or more methyl radicals, are obtained by reaction of a hydroperoxide of formula R—OOH with a compound of formula:

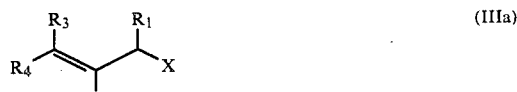

(IIIa)

or

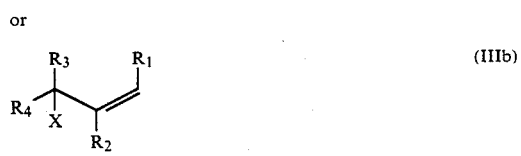 (IIIb)

the operation being carried out in a basic aprotic solvent.

4 Claims, No Drawings

PROCESS FOR THE PREPARATION OF TERPENE PEROXIDES AND PEROXIDES THUS OBTAINED

The present invention provides a process for the preparation of terpene peroxides of the formula:

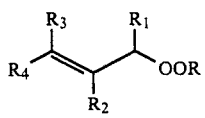   (I)

in which R denotes a tertiary alkyl radical which is unsubstituted or substituted by one or more phenyl radicals, such as a tert-butyl, trityl or cumyl radical, a cycloalkyl radical such as cyclohexyl, or a trialkylsilyl radical such as trimethylsilyl, $R_1$, $R_2$, $R_3$, which are identical or different, each denote a hydrogen atom or an aliphatic radical of 1 to 20 carbon atoms, which is saturated or may contain one or more double or triple bonds and which is unsubstituted or substituted by one or more identical or different inert functional radicals such as, for example, nitro or dialkylamino, and $R_4$ denotes an aliphatic radical of 1 to 20 carbon atoms which is unsubstituted or may contain one or more double or triple bonds and which is unsubstituted or substituted by one or more identical or different inert functional radicals such as, for example, nitro or dialkylamino, or $R_3$ denotes hydrogen and $R_2$ and $R_4$ together form an alkylene radical of 3 or 4 carbon atoms, which is unsubstituted or substituted by one or more methyl radicals.

It is known to prepare mixed organic peroxides by reacting an alkali metal peroxide with a halogenated derivative, the operation being carried out in an alcohol such as methanol, ethanol or isopropanol [U.S. Pat. No. 2,403,709; Campbell et al., J. Amer. Chem. Soc, 1788 (1955); R. Hiatt et al., Can. J. Chem., 450 (1980)] or in a two-phase system by means of phase transfer [B. Maillard et al., Tetrahedron, 5309 (1986); A. A. Turovskii et al., Zhur. Obshchei Khim., 43, 1167 (1973)]. However, the use of these processes results in mixed peroxides with mediocre yields and is frequently accompanied by the formation of undesirable secondary products.

It has now been found, and this is what forms the subject matter of the present invention, that the peroxides of general formula (I) can be obtained by reaction of a hydroperoxide of general formula:

R—OOH   (II)

in which R is defined as above, with a compound of formula:

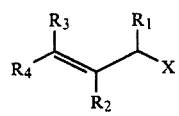   (IIIa)

or

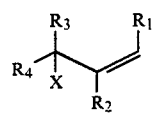   (IIIb)

in which $R_1$, $R_2$, $R_3$ and $R_4$ are as defined above and X denotes an atom or radical which can be replaced by nucleophilic substitution, such as, for example, a halogen (chlorine or bromine) atom or an alkanoyloxy (acetyloxy) radical or an alkyl- or aryl-sulphonyloxy radical (methanesulphonyloxy or p-toluenesulphonyloxy) or a radical —$ONO_2$ or

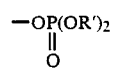

(where R' is alkyl), the operation being carried out in a polar aprotic solvent in the presence of an inorganic base.

The process is generally carried out by adding the compound of formula (IIIa) or (IIIb) to a solution of a hydroperoxide of formula (II) in a homogeneous mixture of a polar aprotic solvent and water in the presence of an inorganic base and at a temperature of between 0° and 50° C., preferably in the neighbourhood of 20° C.

More particularly, the peroxides of general formula (I) are obtained by adding the compound of formula (IIIa) or (IIIb) to a solution of a hydroperoxide of formula (II) in a homogeneous mixture of a polar aprotic organic solvent, such as sulpholane, and water, in the presence of an inorganic base such as potassium hydroxide at a temperature of between 0° and 50° C., and preferably in the neighbourhood of 20° C.

The present invention also provides, as new compounds, the products of formula (I) in which R, $R_1$, $R_2$, $R_3$ and $R_4$ are as defined above, excluding the products of general formula (I) in which, when R denotes tert-butylperoxy (—) O—O—t—Bu) and $R_1$ denotes hydrogen, $R_2$ denotes hydrogen and $R_3$ and $R_4$ are both methyl, or $R_2$ denotes methyl, $R_3$ denotes hydrogen and $R_4$ denotes methyl.

The peroxides of formula (I) are intermediates which are particularly useful in terpene synthesis and which, for example, allow access to intermediates for the preparation of vitamins A and E or for the preparation of perfumes.

Thus, the products of general formula (I) in which $R_1$ and $R_2$ denote a hydrogen atom, $R_3$ denotes a methyl radical and $R_4$ denotes a 4-methylpenten-3-yl radical, that is to say geranyl peroxides, may be employed for the preparation of citral after heating in the presence of an organic base, or tetrahydrogeraniol after complete hydrogenation.

The following Examples illustrate the invention.

EXAMPLE 1

Sulpholane (40 cc) and potassium hydroxide pellets (6.5 g) are introduced into a 250-cc three-necked round-bottomed flask. After cooling to 10° C., a 70% strength aqueous solution of tert-butyl hydroperoxide (12.9 g) is added dropwise. The temperature is maintained at 20° C. for two hours and geranyl chloride (17.2 g, 0.1 mole) is then added dropwise at a temperature of between 10° and 20° C. The solution is kept at 20° C. for 16 hours. After extraction with pentane and purification of the product obtained by flash chromatography, geranyl tert-butyl peroxide (12 g) is obtained, and its structure is confirmed by the infrared spectrum, the mass spectrum and the proton nuclear magnetic resonance spectrum.

The degree of conversion of geranyl chloride is in the neighbourhood of 100% and the yield of geranyl tert-butyl peroxide is in the neighbourhood of 53%.

EXAMPLE 2

Geranyl tert-butyl peroxide (1.13 g, 5 mmol) and n-trioctylamine (5 cc) are introduced into a 25-cc round-bottomed flask. The mixture is heated to 100° C. for 9 hours. After cooling, analysis of the reaction mixture by vapour phase chromatography shows that:

the degree of conversion of geranyl tert-butyl peroxide is in the neighbourhood of 92%, the yield of citral is in the neighbourhood of 12.6%, based on the geranyl tert-butyl peroxide converted.

EXAMPLE 3

Geranyl tert-butyl peroxide (2.26 g, 10 mmol) dissolved in 95% ethanol (40 cc) and palladium on charcoal (10% of palladium; 100 mg) are introduced into an autoclave. The latter is agitated for 4 hours at a pressure of 20 bars of hydrogen. After degassing and filtration, analysis of the reaction mixture by VPC shows that:

the degree of conversion of geranyl tert-butyl peroxide is in the neighbourhood of 100%, the yield of tetra-hydrogeraniol is in the neighbourhood of 72%.

EXAMPLES 4 TO 7

The procedure is as in Example 1 but starting with 1-bromo-3-methyl-2-butene and various hydroperoxides.

The results are collated in Table 1.

TABLE 1

| Example | Hydroperoxide | Yield (%) of mixed peroxide isolated |
|---|---|---|
| 4 | $(CH_3)_3C-O-OH$ | 41% |
| 5 | $C_6H_5-C(CH_3)_2-O-OH$ | 54% |
| 6 | 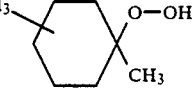 | 37% |
| 7 | $(C_6H_5)_3C-O-OH$ | 46% |

EXAMPLE 8

By following the procedure of Example 1 and replacing geranyl chloride with geranyl bromide, geranyl tert-butyl peroxide is obtained in a 50% yield.

I claim:

1. A process for the preparation of a terpene peroxide of formula:

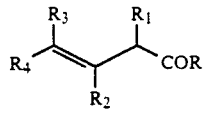

in which: R denotes a tertiary alkyl radical which is unsubstituted or substituted by one or more phenyl radicals, a cycloalkyl radical or a trialkylsilyl radical, $R_1$, $R_2$, and $R_3$, which are identical or different, each denote a hydrogen atom or an aliphatic radical of 1 to 20 carbon atoms which is saturated or contains at least one double or triple bond, and $R_4$ denotes an aliphatic radical of 1 to 20 carbon atoms which contains at least one double or triple bond, which comprises acting a hydroperoxide of formula:

ROOH in which R is as hereinbefore defined, with a compound of formula:

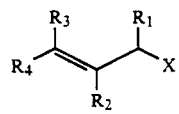

or

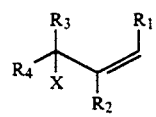

in which $R_1$, $R_2$, $R_3$ and $R_4$ are as hereinbefore defined and X denotes halogen, alkanoyloxy, alkylsulphonyloxy, arylsulphonyloxy, $-ONO_2$ or

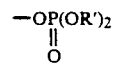

(where R' is alkyl), in a polar aprotic solvent in the presence of an inorganic base at a temperature of between 0° and 50° C.

2. Process according to claim 1 wherein R is t-butyl, cumyl, (3 or 4)-methyl-1-methyl-cyclohexyl, or trityl, X is chlorine or bromine, $R_1$ and $R_2$ are hydrogen, $R_3$ is methyl, and $R_4$ is 4-methyl-penten-3-yl.

3. Process according to claim 1, wherein the polar aprotic solvent is sulpholane.

4. Process according to claim 1, wherein the inorganic base is potassium hydroxide.

* * * * *